United States Patent
Gunst et al.

(10) Patent No.: US 12,071,607 B2
(45) Date of Patent: Aug. 27, 2024

(54) MIDSCALE MODEL FOR ORGANIC GROWTH AND PHASING

(71) Applicant: Lonza Ltd., Visp (CH)

(72) Inventors: John Gunst, Stratham, NH (US); Jonathan Fortin, Newmarket, NH (US); Tristan Wilkins, Newmarket, NH (US)

(73) Assignee: Lonza Ltd., Visp (CH)

( * ) Notice: Subject to any disclaimer, the term of this patent is extended or adjusted under 35 U.S.C. 154(b) by 343 days.

(21) Appl. No.: 16/408,819

(22) Filed: May 10, 2019

(65) Prior Publication Data

US 2019/0367858 A1 Dec. 5, 2019

Related U.S. Application Data

(60) Provisional application No. 62/679,076, filed on Jun. 1, 2018.

(51) Int. Cl.
*C12M 1/00* (2006.01)
*C12M 1/26* (2006.01)

(52) U.S. Cl.
CPC ............ *C12M 29/10* (2013.01); *C12M 1/005* (2013.01); *C12M 1/26* (2013.01); *C12M 21/00* (2013.01); *C12M 23/58* (2013.01); *C12M 47/10* (2013.01); *C12M 47/12* (2013.01)

(58) Field of Classification Search
None
See application file for complete search history.

(56) References Cited

U.S. PATENT DOCUMENTS

| | | | |
|---|---|---|---|
| 5,633,162 A | 5/1997 | Keen et al. | |
| 6,139,746 A * | 10/2000 | Kopf | B01D 15/361 |
| | | | 210/659 |
| 10,053,659 B2 | 8/2018 | Wyatt et al. | |
| 10,589,239 B2 | 3/2020 | Gebauer et al. | |

(Continued)

FOREIGN PATENT DOCUMENTS

| DE | 102015220315 A1 * | 4/2017 | ............ B01F 5/0206 |
|---|---|---|---|
| GB | 2251249 | 7/1992 | |

(Continued)

OTHER PUBLICATIONS

Søren K. Rasmussen. "Recombinant antibody mixtures: Production strategies and cost considerations". Archives of Biochemistry and Biophysics 526. 2012. 139-145. (Year: 2012).*

(Continued)

*Primary Examiner* — Holly Kipouros
*Assistant Examiner* — Nathan G Esperon
(74) *Attorney, Agent, or Firm* — Dority & Manning, P.A.

(57) ABSTRACT

The present disclosure is directed to the organic growth and phasing design for a system for the industrial growth of biologics. A system may include a number of subsystems, such as a buffer distribution subsystem, a media preparation subsystem, a bioreactor subsystem, a harvest subsystem, and/or a purification subsystem. The subsystems may be highly interconnected for flexible process flow design. Additionally, the subsystems may be constructed with a total output capacity with a total number of equipment stations and operated at a lower output capacity with fewer than the total equipment stations to maintain headroom for growth in phases.

23 Claims, 7 Drawing Sheets

(56) References Cited

U.S. PATENT DOCUMENTS

| | | | | |
|---|---|---|---|---|
| 2008/0269468 | A1* | 10/2008 | Vogel | C07K 14/755 530/414 |
| 2011/0117605 | A1* | 5/2011 | Tolstrup | A61P 11/00 435/71.1 |
| 2011/0236932 | A1* | 9/2011 | Stobbe | C12M 23/42 435/71.1 |
| 2011/0258837 | A1 | 10/2011 | Scannon et al. | |
| 2015/0101264 | A1* | 4/2015 | Jornitz | E04H 3/08 52/79.9 |
| 2015/0299644 | A1* | 10/2015 | Tijsterman | C07K 16/00 435/69.6 |
| 2015/0353896 | A1* | 12/2015 | Bruninghaus | C12N 5/00 435/183 |
| 2016/0010883 | A1* | 1/2016 | Jornitz | F24F 3/167 29/897.3 |
| 2016/0083454 | A1* | 3/2016 | Duthe | C07K 1/16 530/388.26 |
| 2016/0097074 | A1 | 4/2016 | Collins et al. | |
| 2016/0145563 | A1* | 5/2016 | Berteau | C12M 41/48 137/15.01 |
| 2016/0289633 | A1 | 10/2016 | Yang et al. | |
| 2017/0058244 | A1 | 3/2017 | Labarge et al. | |
| 2017/0137764 | A1* | 5/2017 | Punchard | C12M 29/26 |
| 2017/0218012 | A1* | 8/2017 | Konstantinov | C12M 47/12 |
| 2017/0260763 | A1 | 9/2017 | Fortin et al. | |
| 2017/0369828 | A1 | 12/2017 | Mietzner et al. | |
| 2018/0037861 | A1 | 2/2018 | Wilkins | |
| 2018/0320121 | A1 | 11/2018 | Sitek et al. | |
| 2018/0320124 | A1* | 11/2018 | Müller-Auffermann | B01F 25/50 |
| 2019/0275519 | A1* | 9/2019 | Castillo | C12N 7/00 |
| 2019/0352595 | A1 | 11/2019 | Grimm et al. | |

FOREIGN PATENT DOCUMENTS

| | | | | |
|---|---|---|---|---|
| WO | WO 90/03430 | | 4/1990 | |
| WO | WO-2017067885 | A1 * | 4/2017 | B01F 5/0206 |

OTHER PUBLICATIONS

Sinclair and Monge. "Concept Facility Based on Single-Use Systems, Part 2". BioProcess International. Oct. 2005. https://www.semanticscholar.org/paper/Concept-Facility-Based-on-Single-Use-Systems%2C-Part-Sinclair-Monge/79a913b213c8b89cb9928f9582480f557172cb64 (Year: 2005).*

Sinclair and Monge. "Biomanufacturing for the 21st Century: Designing a Concept Facility Based on Single-Use Systems" BioProcess International. Oct. 2004. https://www.semanticscholar.org/paper/Biomanufacturing-for-the-21-st-Century-Designing-a-Sinclair-Monge/b283f77d4b78e8e10962b4be6b4216973537a446 (Year: 2004).*

PCT/US2019/031975, Search Report and Written Opinion dated Nov. 26, 2019, 16 pages.

Brandon Patterson, "A Closer Look at Automated In-Line Dilution" BioPharm International, Oct. 1, 2009, 8 pages.

Gronemeyer, Ditz and Strube, "Trends in Upstream and Downstream Process Development for Antibody Manufacturing", Bioengineering, Oct. 2014, 1, 188-212.

Downstream Processing, Chapter 11, Introduction to Biomanufacturing, pp. 424-456.

Bsargent, Perfusion Bioreactors—With so much to offer they deserve a closer look, Jun. 12, 2013, 6 pages, http://cellculturedish.com/2013/06/perfusion-bioreactors-with-so-much-to-offer-they-deserves-a-closer-look/.

Benjaminminow, et al., Implementing a Fully disposable MAb Manufacturing Facility, Jun. 1, 2012, 13 pages.

Faster to Market: Aseptic Filing Workcells within prefabricated modular fill-finish cleanrooms, Jan. 25, 2017, 4 pages, Blog (https://vanrx.com/category/blog/), Featured (https://vanrx.com/category/featured/).

Multiplexing sterile injectables manufacturing, Jun. 5, 2017,https://vanrx.com/news, Blog (https://vanrx.com/category/blg/).

* cited by examiner

MIDSCALE MODEL FOR ORGANIC GROWTH AND PHASING

RELATED APPLICATIONS

The present application is based on and claims priority to U.S. Provisional Patent application Ser. No. 62/679,076, filed on Jun. 1, 2018, which is incorporated herein by reference.

BACKGROUND

The pharmaceutical industry has traditionally focused significant attention on so-called blockbuster drugs, which may demand significant investment in permanent facilities dedicated to a single process. Once established, the efficiency of a single process flow can provide strong return on the initial investment.

However, market factors demand industrial processes with increased flexibility at a reduced cost. In particular, an increasing need for specialized pharmaceuticals have highlighted the shortcomings of facilities designed around a single dominant product line. The pressures for quality control and extensive development and refinement may require multiple revisions or iterations of a particular process flow.

For example, various biologic cell culture processes may be used to extract useful organic components, such as proteins, enzymes, metabolites, or other biomass. Such processes are often time consuming and require significant capital investment to construct a single facility to execute the culturing and growth process. In many cases, existing facilities, previously configured for one product, may not be easily or quickly reconfigured to support iterations of a new product in a trial capacity or in a production capacity.

Furthermore, when the production stage is reached, existing equipment is not easily reconfigured to expand upon the initially small product yields. However, traditional high-yield facilities may not be suitable for the initial stages of development, becoming inefficient when subjected to rapidly changing product cycles.

In view of the above, a need exists for a flexible production line that may rapidly adapt and grow based on needs, allowing for fast reconfiguration, greater throughput, and greater product diversity. There is a further need for flexibility in both the process and equipment design as well as the facility and building designed to contain the process. In summary, a need exists for an organic growth and phasing design for the industrial growth of biologics.

SUMMARY

In general, the present disclosure is directed to a system for the growth of biologics. The system includes a bioreactor subsystem comprising at least two bioreactors and at least two harvest subsystems. Each harvest subsystem is in fluid communication with each of the bioreactors in the bioreactor subsystem, alone or in combination.

In some embodiments, the system includes a flow control assembly positioned in between the at least two bioreactors and the at least two harvest subsystems. The flow control assembly may be configured to selectively control flow of a fluid from a first bioreactor to a first harvest subsystem and from the first bioreactor to a second harvest subsystem. The flow control assembly may also be configured to control flow of a fluid from a second bioreactor to the first harvest subsystem and from the second bioreactor to the second harvest subsystem.

In some embodiments, the system also includes at least one purification subsystem. Each purification subsystem is in fluid communication with each of the harvest subsystems, alone or in combination. In some embodiments, at least one of the purification subsystems is configured to produce a different biologic than at least one other purification subsystem.

In some embodiments, the system as disclosed herein may be configured to process more than 100 batches per year.

In some embodiments, at least one of the bioreactors is 6000 L or larger. In some embodiments, the bioreactor subsystem comprises a seed train of fed-batch bioreactors and/or at least one perfusion seed train. In some embodiments, a perfusion seed train may feed at least one fed-batch bioreactor.

The present disclosure is also generally directed to a system for buffer distribution including at least one buffer dilution device which accepts at least two inputs (i) and (ii), wherein (i) is a buffer concentrate source stream and (ii) is a water for injection source stream. The system also includes at least one buffer dilution device which delivers a buffer mixture comprising (i) and (ii) to a buffer mixture distribution manifold. At least one buffer mixture distribution manifold may be used to control parameters of the buffer mixture delivered to each of a plurality of destinations independently, the parameters including at least one of the following: flow rate or concentration. The buffer mixture is not stored before delivery to any of the plurality of destinations.

In one embodiment, the system for buffer distribution also includes a first buffer dilution device. The buffer mixture output from the first buffer dilution device is delivered to at least one downstream buffer dilution device as input (i). The input (i) of any buffer dilution device downstream of the first buffer dilution device may be partially diverted to another buffer dilution device or to at least one buffer mixture distribution manifold. At least two buffer mixture distribution manifolds distribute buffer of a different concentration.

In some embodiments, at least two buffer dilution devices deliver buffer of about the same concentration to at least one buffer distribution manifold.

In some embodiments, at least one buffer destination comprises a media preparation subsystem, a cell culture subsystem, a bioreactor subsystem, a harvest subsystem, and/or a purification subsystem.

The present disclosure is also generally directed to a system for the growth of biologics including a perfusion seed train, a bioreactor subsystem containing at least one bioreactor fed from the perfusion seed train in whole or in part, and at least two harvest subsystems. Each harvest subsystem may be configured to receive the effluent of each of the bioreactors in the bioreactor subsystem, alone or in combination.

The present disclosure is also generally directed to a building containing any of the previously described systems. For example, in one embodiment, a building may contain at least two purification subsystems, where each purification subsystem includes three chromatography column stations and three chromatography skid stations in a first room, a chromatography column station and a chromatography skid station in a second adjacent room, and a maintenance area accessible from either the first room or the second room. The maintenance area is accessible from the first and second rooms by airlocks and is further accessible from the remainder of the building by another airlock.

In some embodiments, the second room further includes a filling device.

In some embodiments, the bioreactor subsystem includes a plurality of bioreactor stations in one room, wherein some or all of the stations are filled with a bioreactor. In some embodiments, at least one bioreactor station is not filled with a bioreactor. In some embodiments, at least one of the bioreactor stations not filled with a bioreactor and at least one of the bioreactor stations filled with a bioreactor are configured to maintain fluid communication with a flow control assembly. The flow control assembly may be configured to selectively control the flow of a fluid from any one of at least two bioreactor stations to any one of at least two harvest subsystems.

In some embodiments, a building prepared as herein also includes logistics corridors, personnel areas, packing areas, shipping areas, and/or receiving areas, and may be configured to meet Leadership in Energy and Environmental Design certification standards. The building may also include a plurality of motion, temperature, and/or moisture sensors distributed on, in, and/or around equipment in the building as well as a monitoring system configured to track the outputs of the plurality of sensors and generate records and/or alerts responsive to outputs departing from predetermined ranges.

The present disclosure is also generally directed to a process for the growth of biologics. The process includes growing a cell mass; harvesting material comprising (i) the cells or (ii) components of the cells; passing a first portion of the harvested material to a first purification subsystem; passing a second portion of the harvested material to a second purification subsystem; producing a first product via the first purification subsystem; and producing a second product via the second purification subsystem.

BRIEF DESCRIPTION OF THE FIGURES

A full and enabling disclosure of the present disclosure is set forth more particularly in the remainder of the specification, including reference to the accompanying figures, in which.

Figure 1:
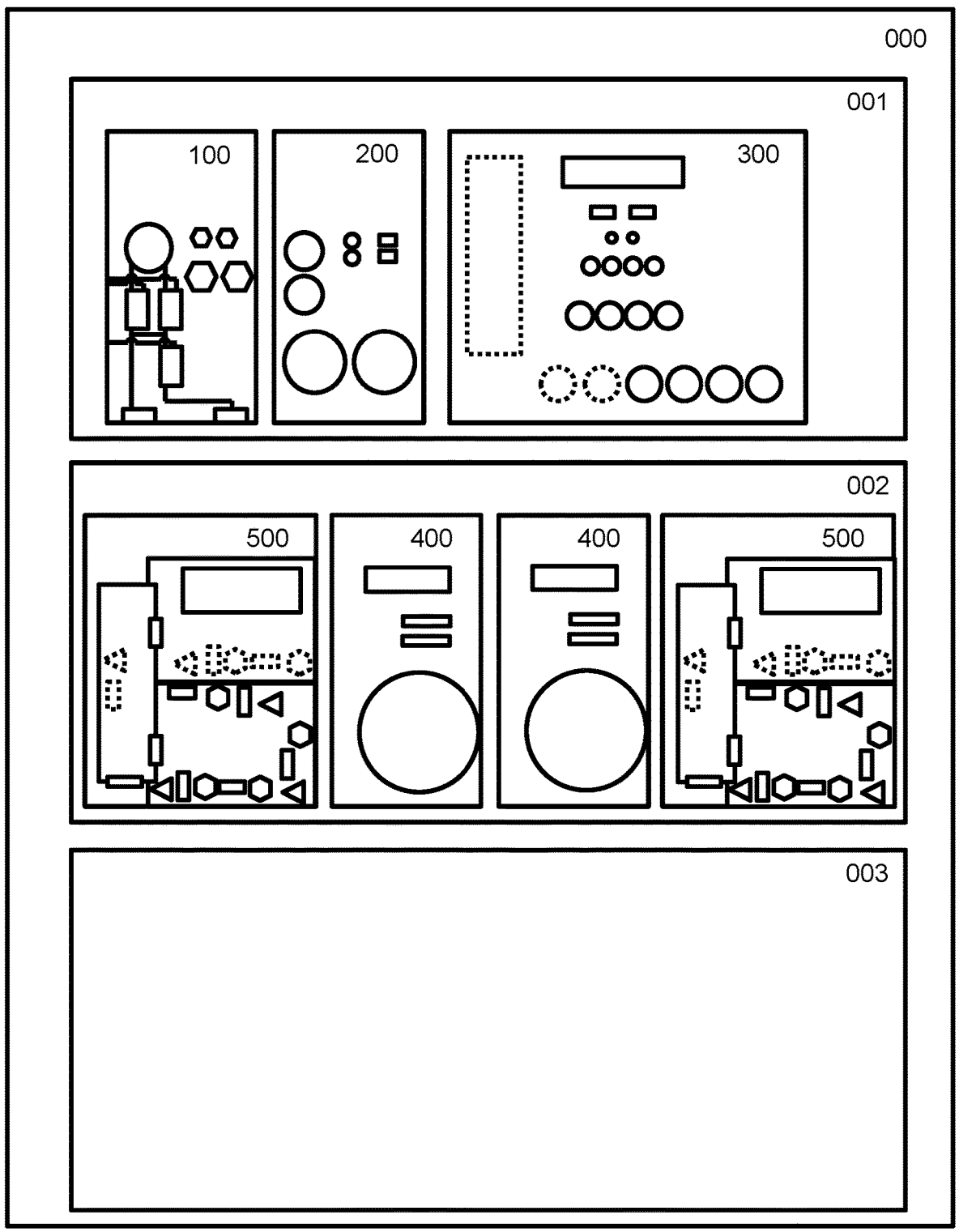
FIG. 1 contains an example layout of a facility prepared as herein.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only and is not intended as limiting the broader aspects of the present disclosure.

In general, the present disclosure is directed to a system for the growth of biologics. As used herein, the growth of biologics refers generally to the process of culturing, feeding, and processing biological material to achieve a particular purpose. In some cases, the purpose is the capture of the grown material itself. For example, a particular cell culture may be desired for its therapeutic use, and the growth process expands a given amount of the cell culture and harvests, washes, and perhaps packages the desired cells. In other cases, some byproduct of the biological mass is desired. For example, in some cases, a protein product of a particular cell culture is desired, and the growth process expands a given amount of the cell culture and extracts, purifies, and perhaps packages the protein product.

The system can be described as a collection of organized subsystems. These subsystems may be organized in a single building or facility. When required, the facility may be constructed to meet standards for controlled and/or classified spaces, as defined by ISO 14644-1, FED STD 209E, and/or EU Good Manufacturing Practice (GMP) standards. By way of example only, reference may be made to single-use equipment. It is to be understood that reusable equipment falls within the scope of the present disclosure.

A flexible process according to the present disclosed may be housed in a facility 000 shown in FIG. 1. The example facility may be divided into three subfacilities: an upstream subfacility 001, a downstream subfacility 002, and a staff subfacility 003. Multiple of any of the subfacilities may be present. The subfacilities may be constructed to be adjacent or stacked, such as on separate floors of a building. For example, the upstream subfacility 001 may reside on a second floor while a downstream subfacility 002 may reside on a first floor. Alternatively, the subfacilities may be housed in distinct but adjacent buildings. In some examples, the upstream and downstream subfacilities are located in distinct subdivisions of a building (e.g., rooms or floors) while the staff subfacility 003 may be located in, around, between, below, and/or alongside the upstream and/or downstream subfacilities.

In one embodiment, as shown in FIG. 1, the upstream subfacility 001 contains a buffer distribution subsystem 100, a media preparation subsystem 200, and a bioreactor subsystem 300; the downstream subfacility 002 contains two harvest subsystems 400 and two purification subsystems 500; and the staff subfacility 003 may contain logistics corridors, personnel areas, packing areas, shipping areas, and/or receiving areas, for example.

In some embodiments, the facility 000 is located in the same building as other facilities used for the production of other products. For example, multiple facilities 000 may be co-located for the production of a plurality of biologics.

Of particular advantage, a single facility 000 may also produce any number of biologics within its enclosed subsystems. For example, the subsystems within the facility may be highly interconnected. In one embodiment shown in FIG. 1, the effluent of the bioreactor subsystem 300 may be in fluid communication with both of the harvest subsystems 400 independently. Additionally, any one of the harvest streams from any one of the harvest subsystems 400 may be in fluid communication with any one or both of the purification subsystems 500. The buffer mixture generated in the buffer distribution subsystem 100 may be directed to any one of the other subsystems. In this manner, a single facility 000 may provide the utmost flexibility for configuring one or more desired process flows.

Fluid communication, as used herein, indicates a direct and intentional connection via some variety of conduit or conduits whereby fluid may flow from one point to another. The fluid communication may be regulated by any number of valves, manifolds, or controllers.

For example, in one embodiment, a flow control assembly may provide a framework for interconnected fluid communication. In some cases, a flow control assembly may be a system of pipes. Some embodiments may also employ any number of valves, diverters, throttles, meters, or manifolds, each optionally controllable manually and/or in an automated fashion. In this manner, a flow control assembly may facilitate the fluid communication between any number of subsystems or locations with subsystems of a facility 000.

A flow control assembly may be selective in its flow control. For example, when a flow control assembly is used to provide fluid communication between a single bioreactor subsystem 300 having two or more bioreactors and two or more harvest subsystems 400, the flow control assembly may selectively control the effluent from any subset of the bioreactors individually, directing each subset to one or more destination harvest subsystems individually chosen for the effluent with flow parameters similarly individually customized. In this manner, the flow control assembly may provide a highly flexible fluid communication network between all or any subset of the bioreactors in the bioreactor subsystem 300 to all or any subset of a plurality of harvest subsystems 400. In some embodiments, a similar flow control assembly may enable the selective and individually controlled distribution of buffer throughout a facility 000 to any number of subsystems.

A flexible embodiment of a facility 000 may, in some examples, contain a fluid connection network between a plurality of subsystems. The subsystems may be arranged and rearranged at different locations within the facility and the fluid connection network infrastructure (e.g., containing a flow control assembly) may permit rapid reconnection of the equipment.

Advantageously, a fluid connection network is created to service more subsystems than initially constructed. For example, a facility 000 as in FIG. 1 may include a fluid connection network that is fully configured to provide fluid connections between one bioreactor subsystem 300 and two harvest subsystems 400, but is only initially operated with one harvest subsystem 400.

Such an interconnected facility 000 may operate in parallel, in whole or in part; for example, the total product train may or may not be completely parallelized. In one embodiment, a number of parallel bioreactor subsystems 300 may feed a single harvest subsystem 400 which feeds a number of parallel purification subsystems 500. In another example, a single bioreactor subsystem 300 feeds a plurality of harvest subsystems 400 which feed a plurality of purification subsystems 500. In this manner, a single facility 000 may produce a number of different products or a number of grades of the same product; for example, a single harvest subsystem 400 may provide the same harvested culture to two purification subsystems 500, one optimized for quality and one optimized for yield. Similarly, various test scenarios may be run in parallel to observe different process effects on the exact same source batch.

Although a facility prepared according to the present disclosure has the capability being optimized to maximize output, the subsystems may be configured independently to achieve any desired output requirements. For example, different purification trains may be adjusted with different operating outputs to minimize surplus product. Additionally, some embodiments may intentionally operate at less than total capacity in order to temporarily lower operating costs when maximum output is not required.

In some embodiments, the total output of the facility 000 may be greater than about 50 batches per year, such as greater than about 75 batches per year, such as greater than about 100 batches per year, such as greater than about 150 batches per year, such as greater than about 300 batches per year. Generally, however, facilities 000 may be scaled to produce less than about 1000 batches per year.

The facility 000 may require an operating staff, perhaps in some cases a large operating staff. In some examples, however, the facility 000 may be partially or completely automated. For example, predictive analytics technology (PAT) may enable streamlined maintenance and monitoring procedures. For example, a number of sensors, such as vibration sensors, noise sensors, moisture sensors, temperature sensors, or power draw sensors may provide a monitoring system with a picture of the operational health of the facility 000. For example, vibration and temperature sensors may be mounted on equipment casings. If any output of any of the sensors departs from a predetermined range, or alternatively a range interpreted by the monitoring system to be ordinary or stable, the monitoring system may generate alerts to indicate a need for attention in a particular area of the facility 000, such as in a particular subsystem. In this manner, the total operational staff required may be reduced.

Advantageously, the flexibility of a facility 000 prepared as herein enables quick recovery from unplanned equipment downtime. For example, if one of two harvest subsystems 400 were to go offline, the interconnected fluid communication network would allow the effluent of the bioreactor subsystem 300 to be quickly and easily redirected to a second harvest subsystem 400.

Due to the highly flexible nature of facilities 000 prepared according to the present disclosure, the facilities may be constructed to be energy efficient. For example, by selectively operating various subsystems only as needed to meet demand, the total utilities consumption may be optimized to be efficient. In some embodiments, the buildings enclosing the facility may be constructed to meet various standards, such as Leadership in Energy and Environmental Design certification standards.

Figure 2:
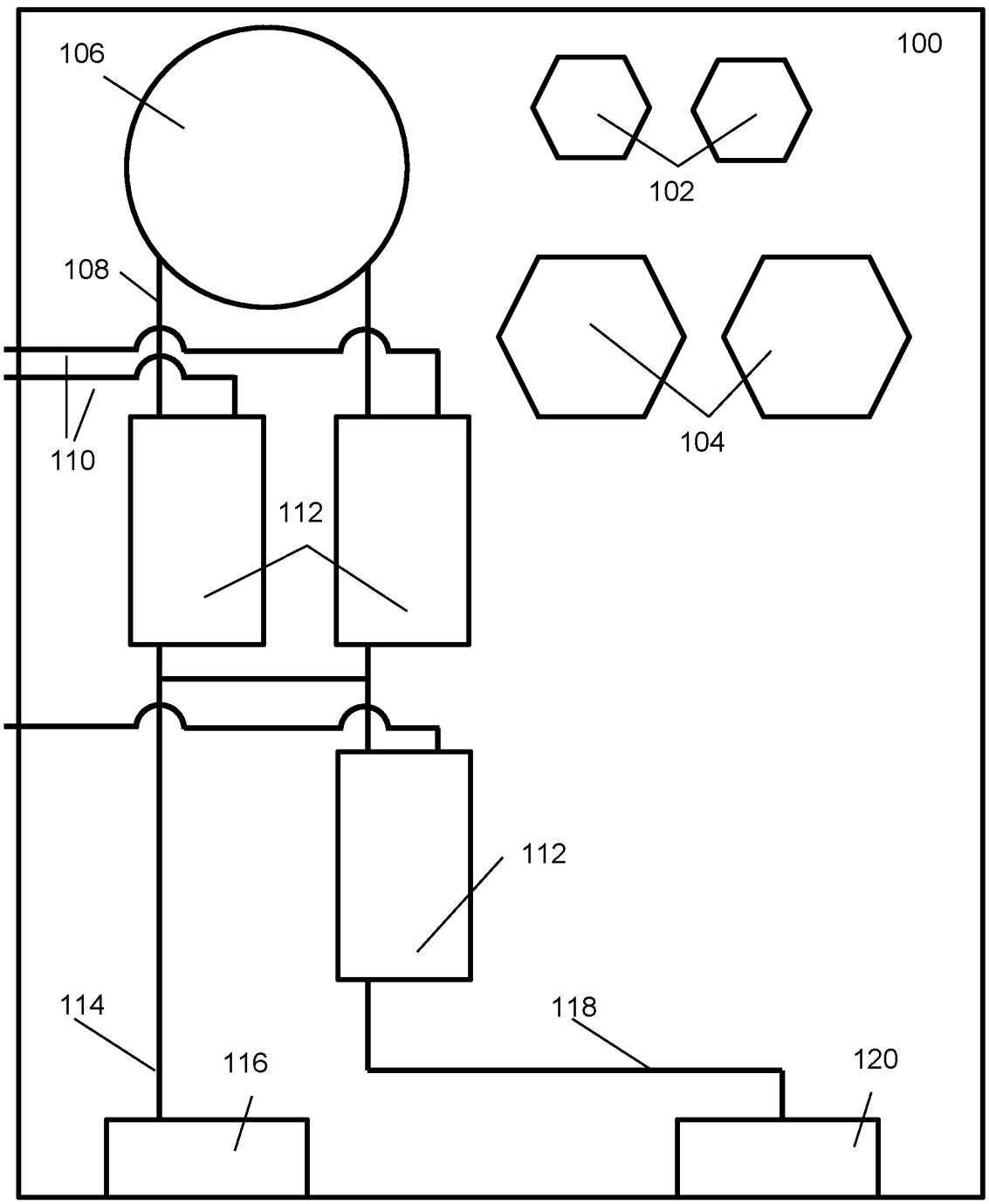
FIG. 2 contains a schematic of a buffer distribution subsystem.

In one embodiment, the system contains a buffer distribution subsystem 100 shown in FIG. 2. A buffer solution may be, for example, a salt solution used to alter or maintain a given pH level in a target environment, such as a bicarbonate solution. For example, buffer may be added to bioreactor feed media to attain and/or maintain a particular pH. The area in which buffer is prepared may be a controlled airspace, such as ISO 8/Grade C/Class 100,000.

Buffer may be mixed and subsequently stored in large tanks before delivery to a target environment. However, in some embodiments, a buffer concentrate may be mixed, for example, in a small single use mixer (SUM) 102 or a large SUM 104. If used, the small and/or large SUM may be various sizes. For example, the small SUM may be larger than about 100 L, such as larger than about 500 L, such as larger than about 1000 L. Generally, however, the small SUM may be smaller than about 3000 L, such as smaller than about 1000 L. A large SUM for buffer concentrate preparation may be larger than about 500 L, such as larger than about 1000 L, such as larger than about 2000 L, such as larger than about 3000 L. Generally, however, the large SUM may be smaller than about 4000 L, such as smaller than about 3000 L.

The ingredients of the buffer may be selected appropriately for a given application. In some embodiments, the processing solution is a buffer such as Tris, Tricine, HEPES, MOPS, PIPES, TAPS, bicine, BES, TES, cacodylate, MES, acetate, MKP, ADA, ACES, glycinamide and acetamidoglycine or acetic acid.

In some embodiments, a bicarbonate buffer may be desired. For example, sodium carbonate and sodium bicarbonate may be provided in dry form and mixed with water for injection. Dry ingredients may be deposited by automated equipment or manually.

The buffer may be stored in a concentrated form in a holding tank 106. The holding tank may be of any useful configuration. For example, the holding tank may be a stainless steel vessel. In other embodiments, the holding tank may contain one or more single-use bags.

A stored concentrate may then be pumped to a buffer dilution device 112. A buffer dilution device 112 may accept the buffer concentrate stream 108 and a sterile water for injection stream 110. In some embodiments, a buffer mixture stream 114 proceeds directly to a buffer mixture distribution manifold 116 after a single dilution stage.

In some embodiments, a buffer mixture stream is directed into a second buffer dilution device 112 which dilutes the buffer mixture stream into a second buffer mixture stream 118. The second buffer mixture stream 118 may be distributed by a second buffer mixture distribution manifold 120. In this manner, the buffer distribution subsystem 100 may produce and distribute buffer solutions having any number of different concentrations.

In some embodiments, more than one buffer dilution device 112 produces buffer of the same concentration. Such embodiments are resistant to downtime due to system malfunction or maintenance, and may also enable increased flexibility to fluctuating buffer demand.

In one embodiment, the buffer mixture distribution manifold 116 controls the flow rate of the buffer mixture to any number of destinations. In some embodiments, the buffer mixture distribution manifold controls the flow of buffer mixture to a plurality of destinations individually, optionally automated to be responsive to sensor feedback indicating target parameters, such as the pH of the destination environment.

The buffer mixture distribution manifold may optionally be centrally located to enable compact and efficient routing of buffer distribution lines to any number of destinations. In some embodiments, some destinations may also be manifolds intended for localized distribution. For example, a central manifold may pump buffer to a particular room of a processing facility and a smaller manifold within the room may distribute the buffer to devices in the room requiring a buffered solution.

Figure 3:
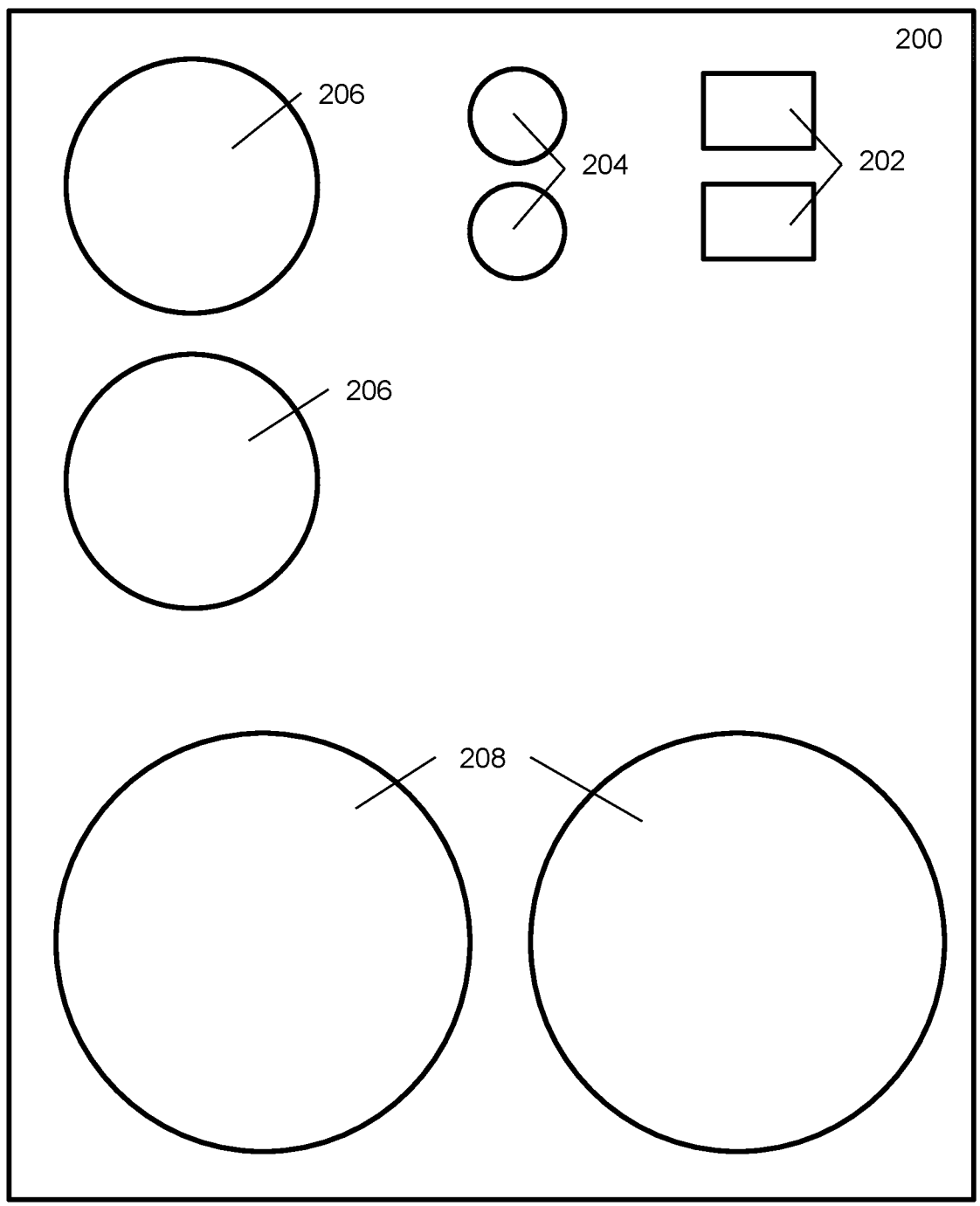
FIG. 3 contains a schematic of a media preparation subsystem.

In some embodiments, a system prepared according to the present disclosure contains a media preparation subsystem 200, as shown in FIG. 3. In general, a media preparation subsystem 200 prepares a substrate on which the inoculated biologic material feeds. For example, media may include sugars, yeasts, sulfates, chlorides, or other suitable feed materials. The media may be prepared in a controlled airspace, such as under ISO 8/Grade C/Class 100,000 conditions.

In some embodiments, the media preparation subsystem 200 involves manual preparation of components. In some embodiments, components may be refrigerated in the media preparation subsystem 200. Prepared media may be refrigerated after mixing for a longer shelf life.

Media may be prepared according to the requirements of any given application. The media may be defined, synthetic, undefined, or basal. The media may be enriched or highly enriched. The media may contain various amino acids, such as non-essential amino acids and essential amino acids, such as glutamine and branched-chain amino acids. The concentration of the media may be varied to manipulate the response of the intended cell culture.

Media components include, for example, buffer, amino acid content, vitamin content, salt content, mineral content, serum content, carbon source content, lipid content, nucleic acid content, hormone content, trace element content, ammonia content, co-factor content, indicator content, small molecule content, hydrolysate content and enzyme modulator content.

Minerals that are optionally present include bismuth, boron, calcium, chlorine, chromium, cobalt, copper, fluorine, iodine, iron, magnesium, manganese, molybdenum, nickel, phosphorus, potassium, rubidium, selenium, silicon, sodium, strontium, sulfur, tellurium, titanium, tungsten, vanadium, and zinc. Exemplary salts and minerals include $CaCl2$ (anhydrous), $CuSO4$ $5H2O$, $Fe(NO3).9H2O$, $KCl$, $KNO3$, $KH2PO4$, $MgSO4$ (anhydrous), $NaCl$, $NaH2PO4H2O$, $NaHCO3$, $Na2SE3$ (anhydrous), $ZnSO4.7H2O$; linoleic acid, lipoic acid, D-glucose, hypoxanthine 2Na, phenol red, putrescine 2HCl, sodium pyruvate, thymidine, pyruvic acid, sodium succinate, succinic acid, succinic acid.Na.hexahydrate, glutathione (reduced), para-aminobenzoic acid (PABA), methyl linoleate, bacto peptone G, adenosine, cytidine, guanosine, 2'-deoxyadenosine HCl, 2'-deoxycytidine HCl, 2'-deoxyguanosine and uridine.

For example, suitable media and culture methods for mammalian cell lines are well-known in the art, as described in U.S. Pat. No. 5,633,162 for instance. Examples of standard cell culture media for laboratory flask or low density cell culture and being adapted to the needs of particular cell types are for instance: Roswell Park Memorial Institute (RPMI) 1640 medium (Morre, G., The Journal of the American Medical Association, 199, p. 519 f. 1967), L-15 medium (Leibovitz, A. et al., Amer. J. of Hygiene, 78, 1p. 173 ff, 1963), Dulbecco's modified Eagle's medium (DMEM), Eagle's minimal essential medium (MEM), Ham's F12 medium (Ham, R. et al., Proc. Natl. Acad. Sc. 53, p288 ff. 1965) or Iscoves' modified DMEM lacking albumin, transferrin and lecithin (Iscoves et al., J. Exp. med. 1, p. 923 ff., 1978). It is known that such culture media can be supplemented with fetal bovine serum (FBS, also called FCS), the latter providing a natural source of a plethora of hormones and growth factors. Cell culture of vertebrate and mammalian cells, respectively, has become a routine matter and is covered in detail, for example, in R. Ian Fresney, Culture of Animal cells, a manual, 4th edition, Wiley-Liss/New York, 2000.

In some embodiments, a high-density growth culture medium may be employed. Such high-density growth media can usually be supplemented with nutrients such as all amino acids, energy sources such as glucose, inorganic salts, vitamins, trace elements (defined as inorganic compounds usually present at final concentrations in the micromolar range), buffers, the four nucleosides or their corresponding nucleotides, antioxidants such as Glutathione (reduced), Vitamin C and other components such as important membrane lipids, e.g., cholesterol or phosphatidylcholine or lipid precursors, e.g., choline or inositol. A high-density medium will be enriched in most or all of these compounds, and will, except for the inorganic salts based on which the osmolarity of the essentially isotonic medium is regulated, comprise them in higher amounts (fortified) than the afore mentioned standard media as can be incurred from EP-435 911 A or GB-2251249 in comparison with RPMI 1640. GB-2251249 gives examples of suitable high-density growth media. In some embodiments, a high density cell culture medium comprises acetate in the amounts stated above, possibly in the absence of a butyrate. Additionally, the culture medium may be balanced and fortified in that a majority of amino acids except for Tryptophane are in excess of 75 mg/L in the culture medium. In conjunction with the general amino acid requirement, the joint amounts of Glutamine and Asparagine may, in some examples, be in total in excess of 1 g/L, such as in excess of 2 g/L of high-density culture medium. It goes without saying that the latter more preferred embodiment is less suitable in case of a recombinant cell line transfected with a Glutamine synthetase (GS) vector, in particular after rounds of amplification of the GS gene sequence have taken place. In those cells, an excess of, for example, glutamine jointly from exogenous and endogenous source would lead to production of ammonia, which is to be avoided.

Small amounts of media may be prepared in a biosafety cabinet. A biosafety cabinet, controlled to ISO 5/Grade A/Class 100, offers isolation for preparation of media for small inoculations.

Generally, however, large amounts of media may be prepared continuously or batch-wise in SUMs. For example, batches may be prepared in a number of SUMs in the subsystem, such as in small SUMs 204 or large SUMs 206, or both, as shown in FIG. 3. SUMs used for preparation of media may be larger than about 100 L, such as larger than about 500 L, such as larger than about 1000 L, such as larger than about 2000 L. Generally, however, the SUMs will be smaller than about 4000 L, such as smaller than about 3000 L, such as smaller than about 2000 L.

Buffer solution used in the media preparation subsystem 200 might be directly pumped into the SUMs from the buffer mixture distribution manifold(s). Alternatively, buffer solution may be pumped into a temporary holding tank (e.g., a tote 202) from which the buffer mixture may be fed as needed into the SUMs. Depending on the volume of the SUM and/or the demands of the process, different concentrations of buffer as received from the first and second buffer mixture distribution manifolds may be fed to different SUMs.

Prepared media may be stored in at least one holding tank 208. In some embodiments, prepared media may be stored directly in single-use bags. If needed, the bags may be stored in a cold room to increase the shelf life of the media. In some embodiments, the holding tanks are refrigerated directly.

Figure 4:
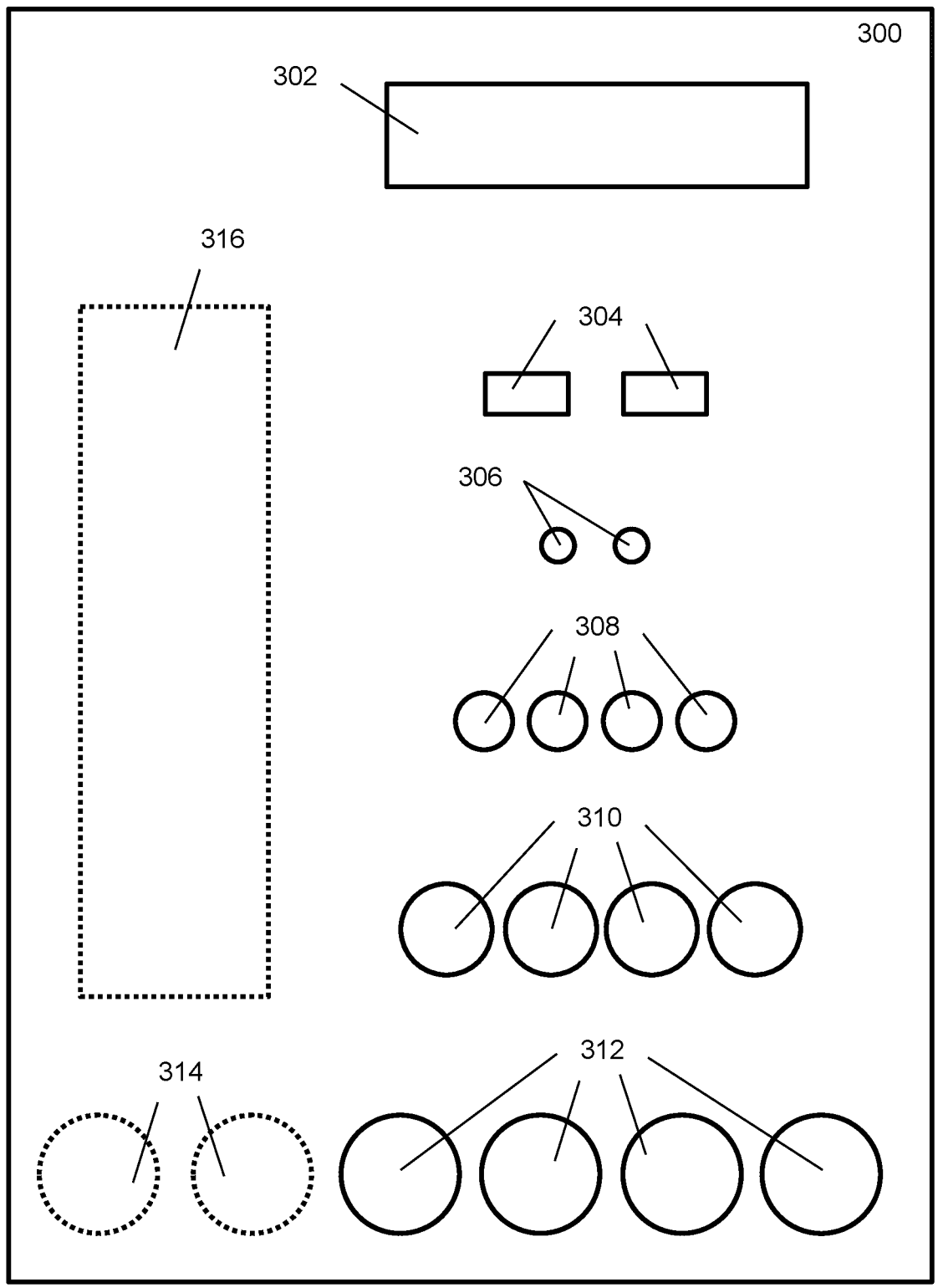
FIG. 4 contains a schematic of a bioreactor subsystem.

In some embodiments, a system prepared according to the present disclosure contains a bioreactor subsystem 300, as shown in FIG. 4. The bioreactor subsystem may be housed in a single room, optionally designated as a Controlled Non-Classified area.

The bioreactor subsystem 300 generally cultures biologics through at least one seed train before placement in at least one production bioreactor. For example, some embodiments start the seed train from a small source, such as a flask or vial prepared by hand in a glove box 302. For example, a flask containing a volume of inoculated media may be hand shaken to start the culturing process in an isolated incubator. In other examples, the process is automated by pumping a small amount of media into a flask pre-filled with the inoculation material.

After inoculation of a small sample, some embodiments transfer the growing cell mass through a number of incubation stages in the seed train. For example, the seed train may progress from a wave incubator 304 (e.g., a perfusion-based wave incubator), to a first single-use bioreactor (SUB) 306 (e.g., 20 L to 500 L), to a second SUB 308 (e.g. 100 L to 1000 L), and to a third SUB 310 (e.g., 500 L to 4000 L) before reaching the production bioreactor 312.

The seed train may progress by manually transferring the active cell mass from one incubation stage to the next. In some embodiments, the transfers may be automated, controlled by feedback from sensors measuring cell mass, cell concentration, glucose levels, or other such progress indicators.

In one embodiment, the seed train contains a perfusion-based reactor system 316 which feeds at least one production bioreactor directly. For example, a perfusion reactor may reduce the time required to grow a cell culture to the size or mass required by the production bioreactors. A perfusion seed train continuously provides fresh media to a cell culture while removing any spent media, retaining the cell culture either in a filtered area or in a holding vessel (e.g., a bioreactor). In this manner, the culture is provided the optimum growing conditions at all times, enabling very high culture concentrations. A perfusion based reactor system 316 may replace one or more intermediate SUB stages in the seed train. For example, in some cases, a perfusion-based reactor system may feed at least one production bioreactor directly, such as two bioreactors, such as three bioreactors, such as five bioreactors. In some cases, all the bioreactors in the bioreactor subsystem 300 may be fed by a perfusion-based reactor system 316. Media and/or buffer may be directly pumped from the media preparation subsystem 200 or the buffer distribution subsystem 100 to the perfusion reaction system 316.

If used in conjunction with a perfusion reactor, bioreactors 312 may or may not be especially designed for perfusion feeding. For example, with regard to the harvest port and tubing design of bioreactors used for perfusion modes of operation, the dip tube needs to be appropriately sized to permit unobstructed flow of culture out of the bioreactor and into a coupled cell retention device and to allow return from the cell retention device back into the bioreactor without foaming and shearing of the cells or cell aggregates. The unimpeded flow of cell culture during perfusion mode or during harvest phase of a fed-batch process is to ensure the cells are not mechanically damaged whilst passing through such tubings, as mechanical damage can result in release of cellular factors (e.g., enzymes such as glutathione reductase, thioredoxin, and thioredoxin reductase or metabolites such as NADPH) which can adversely affect the performance of the process and quality of the product made. Secondly, unimpeded flow of cell culture can result in the culture not becoming hypoxic or anoxic while passing through such tubing and thereby prevent activation of the released cellular factors which can adversely affect the performance process and quality of the product during further processing.

Production bioreactors 312 may include stirred, shaken, airlift, or other bioreactor types. In some embodiments, production bioreactors are continuous, fed-batch, and/or perfusion-fed SUBs. Additionally or alternatively, one or more production bioreactors 312 may be perfusion reactors. In some aspects, the bioreactors can be variable diameter such as those described in U.S. Patent Publication No. 2017/0369828A1, which is hereby incorporated by reference in its entirety.

When more than one production bioreactor 312 is present in the bioreactor subsystem 300, the production bioreactors 312 may be the same or different sizes, such as larger than about 500 L, such as larger than about 1000 L, such as larger than about 2000 L, such as larger than about 5000 L, such as larger than about 8000 L, such as larger than about 12000 L, such as larger than about 18000 L. In one embodiment, the production bioreactors 312 are smaller than about 20000 L, such as smaller than about 15000 L, such as smaller than about 10000 L.

A bioreactor unit can perform one or more, or all, of the following: feeding of nutrients and/or carbon sources, injection of suitable gas (e.g., oxygen), flow of fermentation or cell culture medium, separation of gas and liquid phases, maintenance of growth temperature, maintenance of pH level, agitation (e.g., stirring), and/or cleaning/sterilizing. In one embodiment, the bioreactor is suitable for culturing suspension cells or anchorage-dependent (adherent) cells.

In one embodiment, the bioreactor subsystem 300 is suitable for cell therapy and/or viral therapy operations. In one embodiment, the bioreactor subsystem 300 is suitable for culturing prokaryotic cells or eukaryotic cells. Examples of cells include, but are not limited to, bacterial cells (e.g., E. coli. P. pastoris), yeast cells (e.g., S. cerevisae, T. reesei), plant cells, insect cells (e.g., Sf9), Chinese hamster ovary cells (CHO, and any genetically modified or derived CHO cell line), mouse cells (e.g., mouse embryonic fibroblasts, cells derived from mouse cancer models), human cells (e.g., cells from any tissue or organ, cells from a cancer or other diseased cell line, stem cell), hybridoma cells, or other genetically modified or hybrid cells. In one embodiment, the cells express or produce a product, such as a recombinant therapeutic or diagnostic product. Examples of products produced by cells include, but are not limited to, antibody molecules (e.g., monoclonal antibodies, bispecific antibodies), fusion proteins (e.g., Fc fusion proteins, chimeric cytokines), other recombinant proteins (e.g., glycosylated proteins, enzymes, hormones), or lipid-encapsulated particles (e.g., exosomes, virus-like particles).

The production bioreactors 312 may optionally be located in a bioreactor station 314. For example, a bioreactor station 314 may provide the physical floor, wall, or hanging rack space in a room for placement of a bioreactor, as well as connections for any electrical, mechanical, heated/cooled water, media, buffer, sterile WFI, and/or cell culture conduits required by a bioreactor. For example, each bioreactor station 314 may be in communication with at least one buffer distribution manifold 116 or 120 to provide buffer of the required concentration to the bioreactor.

Additionally or alternatively, a bioreactor station 314 may provide connections for the output of any effluent from a bioreactor. For example, a bioreactor station 314 may be in fluid communication with a flow control assembly. When a station 314 is not filled with a bioreactor, the fluid communication may be controlled by a closed valve, for example. However, any existing fluid communication conduit aids the quick expansion of bioreactor capacity by enabling new bioreactors installed in stations 314 to be easily connected to the flow control assembly without the need to install additional conduits or other pipes with the addition of each new bioreactor.

In some examples, a bioreactor station 314 is uniquely configured to a particular size, type, or configuration of bioreactor. In other examples, each bioreactor station 314 may support a wide variety of bioreactors with little to no customization. In this manner, bioreactor reconfiguration is streamlined. For example, a bioreactor subsystem 300 may be quickly scaled in response to a growing product demand.

In some examples, a production bioreactor 312 is placed in each bioreactor station 314. In other examples, such as shown in FIG. 4, some bioreactor stations 314 do not contain a production bioreactor 312. In such examples, the empty stations stand ready to receive production bioreactors if the added output is required.

The stations 314 may be filled all at one time or may be filled in phases as desired. For example, the bioreactor subsystem may be operated at one time with a first portion of stations filled. At a second time, a second portion of stations may be filled, in addition to or in substitution of the first portion. That is, the first and second portions need not overlap with any number of stations. A bioreactor subsystem 300 may alternate between operating with the first portion and operating with the second portion in order to minimize downtime between bioreactor batches.

In some examples, a second portion of stations may be filled entirely in addition to the first portion, the second portion being equal to or less than the amount of previously unused bioreactor stations 314. For example, a bioreactor subsystem 300 with six bioreactor stations 314 operating with a first portion of four bioreactors 312 initially may add a second portion of two bioreactors 312 if needed. In another example, when titers are below a design threshold, additional bioreactors may be quickly brought online to increase the total bioreactor volume. In this manner, a high-output bioreactor subsystem 300 may be constructed and implemented in phases as the demand ramps up from small scale to large scale.

A bioreactor subsystem 300 may be equipped with more than 1 bioreactor station, such as more than 2, such as more than 5, such as more than 10. In one embodiment, the bioreactor subsystem 300 is equipped with fewer than 30 stations, such as fewer than 20, such as fewer than 10. In some embodiments, the bioreactor subsystem 300 may be operated with fewer than 80% of stations filled, such as fewer than 60%, such as fewer than 40%, such as fewer than 20%. In additional examples, the bioreactor subsystem may be operated with more than 20% of stations filled, such as more than 40%, such as more than 60%, such as more than 80%, even up to 100%. Stations may be filled or deactivated in any number of phases or steps, such as one, two, three, four, or more.

In some embodiments, the production bioreactors may receive media directly from the media holding tanks 208. For example, the media may be distributed to all bioreactor stations 314 containing a production bioreactor 312 via a main line to the bioreactor subsystem 300 subsequently distributed via manifold to each station or via direct lines to each station. The flow in each line may be monitored and/or controlled to ensure optimum operation.

In other examples, media may be manually distributed to each bioreactor station 314 in mobile vessels. For example, a tote or a bag may be filled directly in the media preparation subsystem 200 and transported to the bioreactor subsystem 300. In some embodiments, the media preparation subsystem 200 and the bioreactor subsystem 300 are adjacent, and a pass-through airlock may enable easy transfer. The bioreactor stations may include bins or receptacles for the media-containing tote or bag. In such an example, once the bin or receptacle has been filled, the inflow of media to the bioreactor may be monitored and/or controlled to ensure optimum operation.

For example, the control may follow an open loop (e.g., a timer) or a closed loop (e.g., responsive to feedback from sensors reading temperature, cell density, glucose levels, etc.). The control system may also, in some examples, notify operational staff of the need to refill the media receptacle of the bioreactor station 314.

Figure 5:
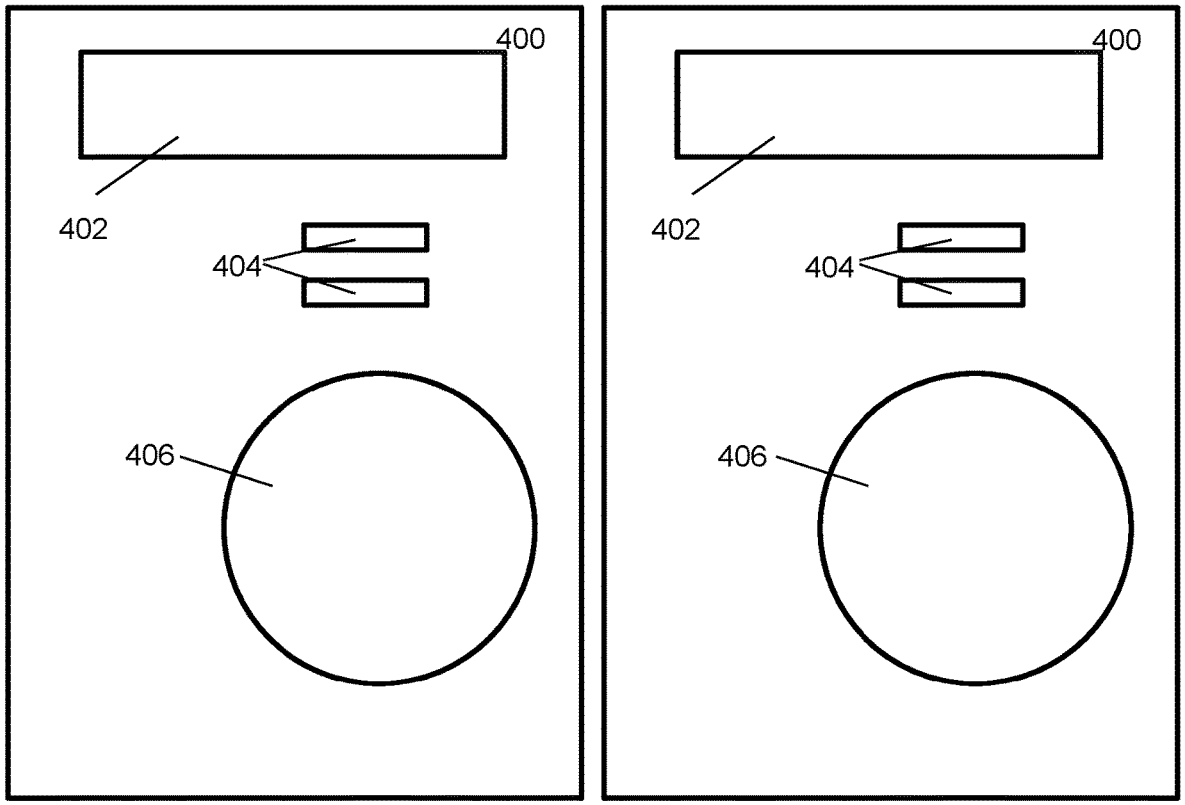
FIG. 5 contains a schematic of a harvest subsystem.

A system prepared according to the present disclosure may, in some embodiments, contain at least one harvest subsystem 400. For example, as shown in FIG. 5, a system may contain two harvest subsystems 400, each having a centrifuge 402 which may receive the effluent of the bioreactor subsystem 300. For example, a centrifuge 402 may remove cells and large cell solids from the bioreactor effluent. The output of the centrifuge 402 may be passed to a series of one or more filtration steps. For example, a bank of depth filters 404 may further clarify the harvest stream and lower the turbidity to a target level. Additionally, depth filters 404 may be electrically charged to reduce other impurities, such as removing endotoxins, virus particles, and/or protein impurities.

After at least one centrifugal, clarification, and/or filtration step, the harvest stream may be directed to at least one harvest tank 406. In some examples, each harvest subsystem 400 contains at least one harvest tank 406. In other examples, two or more harvest subsystems may share at least one harvest tank 406. For example, multiple centrifuges 402 and multiple depth filters 404 may optionally pass effluent to one tank 406. The harvest tank 406 may be connected to at least one buffer mixture distribution manifold 116 or 120 for controlling the pH of the harvest solution. In some examples, multiple harvest subsystems 400, each independently configured, may operate in parallel and be arranged adjacent or removed from each other.

Figure 6:
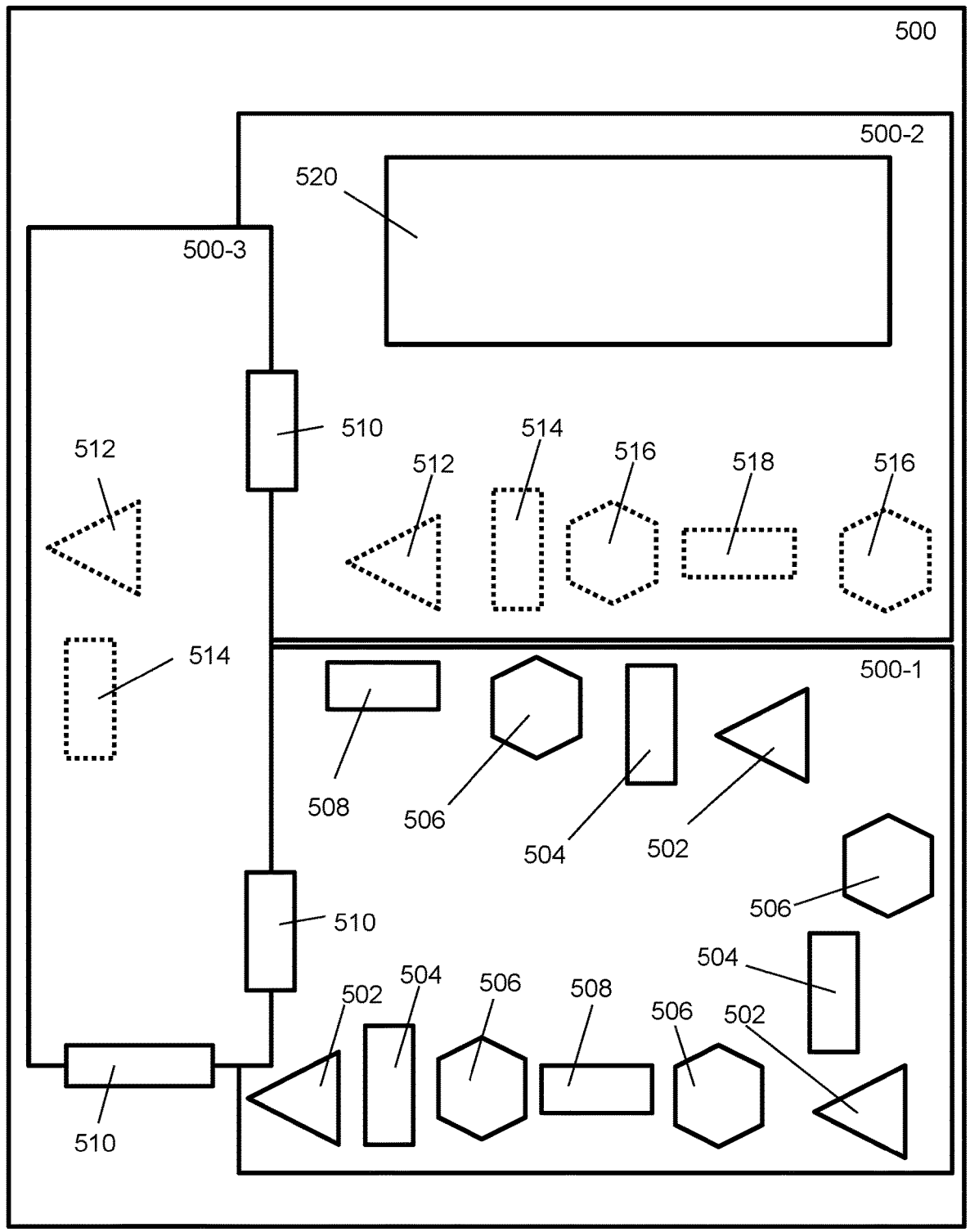
FIG. 6 contains a schematic of a purification subsystem.
Figure 7:
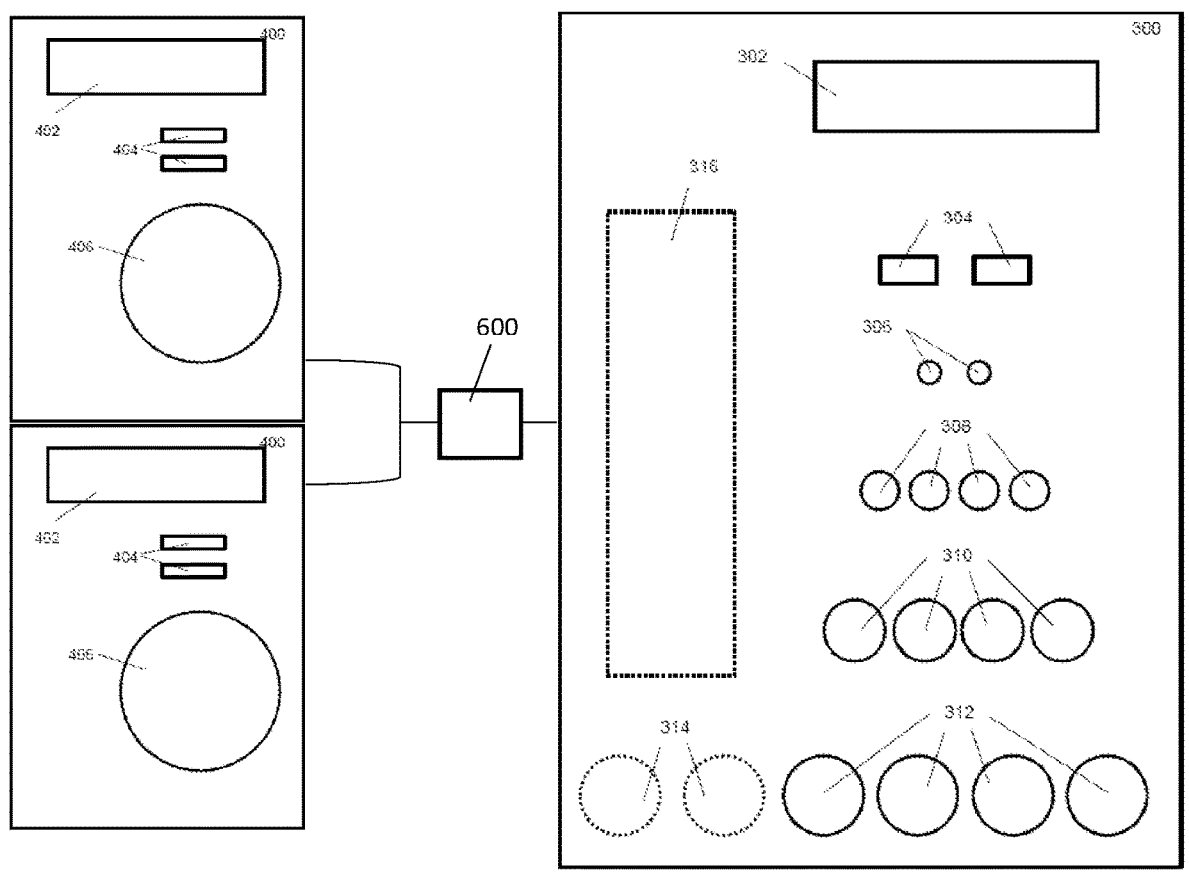

In some embodiments, a system prepared according to the present disclosure contains a purification subsystem 500, as shown in an example embodiment in FIG. 6. In some embodiments, the purification subsystem 500 may be divided into a pre-viral train 500-1 and a post-viral train 500-2. Further, in some embodiments, the system includes a flow control assembly 600 positioned in between the at least two bioreactors of bioreactor subsystem 300 and the at least two harvest subsystems 400 as shown in an example embodiment in FIG. 7.

The pre-viral train 500-1 may include at least one chromatography, filtration, or mixing device.

Methods of 1-dimensional (1D) chromatography suitable for use in the methods described here are known to one of skill in the art and include, for example, affinity chromatography, gel filtration chromatography, ion exchange chromatography, reversed phase chromatography, hydrophobic interaction chromatography. In some embodiments, the one-dimensional chromatography method is HPLC reversed phase chromatography. Chromatography can include high performance liquid chromatography (HPLC), gas chromatography (GC), capillary electrophoresis, ion mobility. See also, for example, Process Scale Purification of Antibodies, Uwe Gottschalk 2011 John Wiley & Sons ISBN: 1118210743; Antibodies Vol 1 Production and Purification, G. Subramanian 2013 Springer Science & Business Media; Basic Methods in Antibody Production and Characterization, Gary C. Howard 2000 CRC Press.

Additional exemplary chromatographic methods include, but are not limited to, Strong Anion Exchange chromatography (SAX), liquid chromatography (LC), high performance liquid chromatography (HPLC), ultra performance liquid chromatography (UPLC), thin layer chromatography (TLC), amide column chromatography, and combinations thereof. Exemplary mass spectrometry (MS) include, but are not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof. Exemplary electrophoretic methods include, but are not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof. Exemplary nuclear magnetic resonance (NMR) include, but are not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

Suitable spectroscopic techniques include, for example, Raman spectroscopy. Raman spectroscopy is a technique that is increasing in popularity among the different disciplines of forensic science. Some examples of its use today involve the identification of drugs (Hodges et al., "The Use of Fourier Transform Raman Spectroscopy in the Forensic Identification of Illicit Drugs and Explosives," Molecular Spectroscopy 46:303-307 (1990)), lipsticks (Rodger et al., "The In-Situ Analysis of Lipsticks by Surface Enhanced Resonance Raman Scattering," Analyst 1823-1826 (1998)), and fibers (Thomas et al., "Raman Spectroscopy and the Forensic Analysis of Black/Grey and Blue Cotton Fibres Part 1: Investigation of the Effects of Varying Laser Wavelength," Forensic Sci. Int. 152:189-197 (2005)), as well as paint (Suzuki et al., "In Situ Identification and Analysis of Automotive Paint Pigments Using Line Segment Excitation Raman Spectroscopy: I. Inorganic Topcoat Pigments," J. Forensic Sci. 46:1053-1069 (2001)) and ink (Mazzella et al., "Raman Spectroscopy of Blue Gel Pen Inks," Forensic Sci. Int. 152:241-247 (2005)) analysis. The theory behind Raman spectroscopy is based on the inelastic scattering of low-intensity, nondestructive laser light by a solid, liquid or gas sample. Very little or no sample preparation is needed, and the required amount of tested material could be as low as several picograms or femtoliters ($10^{-12}$ gram or $10^{-15}$ liter, respectively). A typical Raman spectrum consists of several narrow bands and provides a unique vibrational signature of the material (Grasselli et al., "Chemical Applications of Raman Spectroscopy," New York: John Wiley & Sons (1981)). Unlike infrared (IR) absorption spectroscopy, another type of vibrational spectroscopy, Raman spectroscopy shows very little interference from water (Grasselli et al., "Chemical Applications of Raman Spectroscopy," New York: John Wiley & Sons (1981)), and that makes it a great technique for analyzing body fluids and their traces. Proper Raman spectroscopic measurements do not damage the sample. The stain or swab could be tested on the field and still be available for further use in the lab for DNA analysis, and that is very important to forensic application. The design of a portable Raman spectrometer is a reality now (Yan et al., "Surface-Enhanced Raman Scattering Detection of Chemical and Biological Agents Using a Portable Raman Integrated Tunable Sensor," Sensors and Actuators B. 6 (2007); Eckenrode et al., "Portable Raman Spectroscopy Systems for Field Analysis," Forensic Science Communications 3:(2001)) which would lead to the ability to make identifications at the crime scene.

The types of Raman spectroscopy suitable for use in conjunction with the present disclosure include, but are not limited to conventional Raman spectroscopy, Raman microspectroscopy, near-field Raman spectroscopy, including but not limited to the tip-enhanced Raman spectroscopy, surface enhanced Raman spectroscopy (SERS) and surface enhanced resonance Raman spectroscopy (SERRS), coherent anti-Stokes Raman spectroscopy (CARS), etc. Both Stokes and anti-Stokes Raman spectroscopy can be used.

In some embodiments, a rapid non-invasive test is performed on one or more bioprocessing intermediates using the chromatographic or spectroscopic methods described herein. In some embodiments, the rapid test is performed using Ramon spectroscopy.

In one embodiment shown in FIG. 6, a harvest stream from a harvest tank 406 is delivered to a chromatography skid 504 and its accompanying chromatography column 502. After a first chromatography step, the product stream may be passed to a SUM 506, such as for virus inactivation, before proceeding to a filtration device 508.

A filtration device 508 may include a variety of filtration mechanisms. In some examples, a tangential flow filtration (TFF) device is used. For example, a TFF device may enable the diafiltration of the product stream. In such an example, the TFF device may optionally be connected to at least one buffer mixture distribution manifold 116 or 120 for a buffer exchange or concentration operation. The TFF may optionally work in conjunction with a SUM 506 for recirculation and/or holding of the retentate.

In some embodiments, a TFF process consists of two stages: volume reduction and diafiltration. During the volume reduction step the bulk volume (e.g., cell culture media) is filtered out through the permeate side of the filter until a desired product concentration is reached in the processing bag or holding tank. In a diafiltration stage following the volume reduction stage, the concentrated product is washed with a fluid, such as a buffer, to remove cell culture or harvest media components that are undesired or unacceptable. Further volume reduction may also be carried out after diafiltration to reach a desired product density.

The pre-viral train 500-1 may include any number of chromatography, filtration, mixing, and/or other desired devices. For example, FIG. 6 shows a pre-viral train with three chromatography stages. However, chromatography, filtration, and/or mixing devices may each be present in any quantity, such as 1, 2, 3, 4, 5, 6, 7, 8, 9, 10, or more, such as 20 or 30, each device being present in an amount independently selected.

The post-viral train 500-2 may include any number of desired finishing devices. For example, the post-viral train may include one or more final polishing chromatography and/or filtration stages in addition to or in substitute of the chromatography stages in the pre-viral train 500-1. The critical viral reduction step is considered to be the appropriate point for spatial segregation with the post-viral separation sub-unit to be considered essentially virus free. The post-viral separation sub-unit houses equipment and utilities suitable for any one of the following: ultrafiltration (tangential filtration), normal filtration, chromatography, formulation, titration, mixing, concentration, buffer exchange, bulk drug substance container filling and freezing.

In some examples, the post-viral train may include empty equipment stations, such as a chromatography column station 512, a chromatography skid station 514, a SUM station 516, and/or a TFF device station 518, as shown in FIG. 6. Similar to the bioreactor stations 314, the various stations 512, 514, and 516 may provide the respective devices with the required electrical and mechanical connections for operation, as well as any necessary heated/cooled water, sterile WFI, product stream, buffer, media, filtration media, adsorbent, eluent, or any other input required by the respective devices. For example, a chromatography column station 512 may provide the necessary electrical, adsorbent, eluent, and/or product stream connections while also providing the physical floor, wall, or hanging rack space for mounting.

Similar to as discussed regarding bioreactor stations 314, chromatography column and skid stations may be present in a filled, empty, or deactivated capacity, in any of the exemplary quantities described above, or in other quantities as desired.

Optionally, both the pre-viral and post-viral trains may include equipment installed in an associated station. For example, each chromatography column and skid in the pre-viral train 500-1 may be installed in a column station 512 and a skid station 514, respectively. If the post-viral train also has at least one column station 512 and skid station 514, then any of the chromatography columns or skids in the previral train 500-1 may be easily uninstalled from the pre-viral train 500-1 and quickly installed in the post-viral train 500-2. Optionally, the pre-viral and the post-viral trains may both contain at least one empty station to enable easy and rapid insertion of additional equipment if the need arose. For example, all stations required to support a parallel pre-viral train may be housed in the pre-viral train 500-1 in preparation for future throughput requirements. In this manner, the purification subsystem may quickly and flexibly adapt to growth in phases.

The post-viral train 500-2 may also include some variety of filling device 520. For example, a filling device 520 may be a bottle filling device, or alternatively a bag filling device, or a device filling containers generally. The device may be, in some examples, a self-contained unit, optionally with its own controlled airspace, such as an airspace controlled to ISO 5/Grade A/Class 100.

In some embodiments, a maintenance area 500-3 may be adjacent to one or both of the pre-viral and post-viral trains. When adjacent to both, airlocks 510 permit access from each train as well as from outside the purification subsystem 500. For example the maintenance area 500-3 may be used for equipment cleaning, repair storage, or staging. For example, chromatography columns may be packed and prepared for quick insertion into either the pre-viral or post-viral trains. In some embodiments, the maintenance area 500-3 has both a chromatography column station 512 and a chromatography skid station 514.

The descriptions of the various embodiments of the present disclosure can be utilized in the production of pharmaceuticals and biopharmaceutical products. The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (e.g., siRNA) or DNA (e.g., plasmid DNA), antibiotics or amino acids. In embodiments, the devices, facilities and methods can be used for producing biosimilars.

As mentioned, in embodiments, devices, facilities and methods allow for the production of eukaryotic cells, for example, mammalian cells or lower eukaryotic cells such as for example yeast cells or filamentous fungi cells, or prokaryotic cells such as Gram-positive or Gram-negative cells and/or products of the eukaryotic or prokaryotic cells, for example, proteins, peptides, antibiotics, amino acids, nucleic acids (such as DNA or RNA), synthesized by the eukaryotic cells in a large-scale manner. Unless stated otherwise herein, the devices, facilities, and methods can include any desired volume or production capacity including but not limited to bench-scale, pilot-scale, and full production scale capacities.

In embodiments, the cells are eukaryotic cells (e.g., mammalian cells). The mammalian cells can be for example human or rodent or bovine cell lines or cell strains. Examples of such cells, cell lines or cell strains are, for example, mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, YO, C127, L cell, COS, e.g., COS1 and COS7, QC1-3, HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the POTELLIGENT® CHOK1 SV (Lonza Biologics, Inc.). Eukaryotic cells can also be avian cells, cell lines or cell strains, such as for example, EBX® cells, EB14, EB24, EB26, EB66, or EBv13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable QUALYST TRANSPORTER CERTIFIED™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57BI/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as a yeast cell (e.g., *Pichia* genus (e.g., *Pichia pastoris*, *Pichia methanolica*, *Pichia kluyveri*, and *Pichia angusta*), *Komagataella* genus (e.g., *Komagataella pastoris*, *Komagataella pseudopastoris* or *Komagataella phaffii*), *Saccharomyces* genus (e.g., *Saccharomyces cerevisae*, *cerevisiae*, *Saccharomyces kluyveri*, *Saccharomyces uvarum*), *Kluyveromyces* genus (e.g., *Kluyveromyces lactis*, *Kluyveromyces marxianus*), the *Candida* genus (e.g., *Candida utilis*, *Candida cacaoi*, *Candida boidinii*), the *Geotrichum* genus (e.g., *Geotrichum fermentans*), *Hansenula polymorpha*, *Yarrowia lipolytica*, or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g., *Aspergillus* (such as *A. niger*, *A. fumigatus*, *A. orzyae*, *A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus*, *Ctenomyces*, *Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium*, *Sporotrichum* (such as *S. thermophile*), *Thielavia* (such as *T. terrestris*, *T. heterothallica*), *Trichoderma* (such as *T. reesei*), or *Verticillium* (such as *V. dahlia*)).

In one embodiment, the eukaryotic cell is an insect cell (e.g., Sf9, MIMIC™ Sf9, Sf21, HIGH FIVE™ (BT1-TN-5B1-4), or BT1-Ea88 cells), an algae cell (e.g., of the genus *Amphora*, Bacillariophyceae, *Dunaliella*, *Chlorella*, *Chlamydomonas*, Cyanophyta (cyanobacteria), *Nannochloropsis*, *Spirulina*, or *Ochromonas*), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus*, *Streptomyces Streptococcus*, *Staphylococcus* or *Lactobacillus*. *Bacillus* that can be used is, e.g., the *B. subtilis*, *B. amyloliquefaciens*, *B. licheniformis*, *B. natto*, or *B. megaterium*. In embodiments, the cell is *B. subtilis*, such as *B. subtilis* 3NA and *B. subtilis* 168. *Bacillus* is obtainable from, for example, the *Bacillus* Genetic Stock Center, Biological Sciences 556, 484 West 12th Avenue, Columbus Ohio 43210-1214.

In one embodiment, the prokaryotic cell is a Gram-negative cell, such as *Salmonella* spp. or *Escherichia coli*, such as, for example, TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type CultureCollection (ATCC).

In embodiments, the cultured cells are used to produce proteins, for example, antibodies, for example, monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, for example, BOTOX®, MYOBLOC®, NUEROBLOC, DYSPORT® (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-n1, DL-8234, interferon, BIOGAMMA®, interferon gamma, thymosin alpha 1, tasonermin, DIGIFAB®, VIPERATAB, ECHITAB, CROFAB®, nesiritide, abatacept, alefacept, REBIF®, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, MONONINE®, eptacog alpha (activated), recombinant Factor VIII+VWF, RECOMBINATER, recombinant Factor VIII, Factor VIII (recombinant), ALPHANATE, octocog alpha, Factor VIII, palifermin, INDIKINASE, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, LEUCOTROPIN, molgramostim, triptorelin acetate, histrelin (subcutaneous implant, HYDRON), deslorelin, histrelin, nafarelin, leuprolide sustained release depot (ATRIGEL®), VIADUR® (leuprolide implant), goserelin, EUTROPIN, KP-102 program, somatropin, mecasermin (growth failure), enlfavirtide, Org-33408, insulin glargine, insulin glulisine, insulin (inhaled), insulin lispro, insulin deternir, insulin (buccal, RAPIDMIST), mecasermin rinfabate, anakinra, celmoleukin, 99 mTc-apcitide injection, myelopid, BETASERON®, glatiramer acetate, GEPON, sargramostim, oprelvekin, human leukocyte-derived alpha interferons, BILIVE, insulin (recombinant), recombinant human insulin, insulin aspart, mecasenin, ROFERON-A, interferon-alpha 2, ALFAFERONE, interferon alfacon-1, interferon alpha, AVONEX®, recombinant human luteinizing hormone, dornase alpha, trafermin, ziconotide, taltirelin, diboterminalfa, atosiban, becaplermin, eptifibatide, ZEMAIRA®, CTC-111, SHANVAC-B, HPV vaccine (quadrivalent), octreotide, lanreotide, ancestirn, agalsidase beta, agalsidase alpha, laronidase, prezatide copper acetate (topical gel), rasburicase, ranibizumab, ACTIMMUNE®, PEG-INTRON®, TRICOMIN®, recombinant house dust mite allergy desensitization injection, recombinant human parathyroid hormone (PTH) 1-84 (sc, osteoporosis), epoetin delta, transgenic antithrombin III, GRANDITROPIN, VITRASE®, recombinant insulin, interferon-alpha (oral lozenge), GEM-21S®, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, BIOJECTOR 2000), VGV-1, interferon (alpha), lucinactant, aviptadil (inhaled, pulmonary disease), icatibant, ecallantide, omiganan, AUROGRAB, pexiganan-acetate, ADI-PEG-20, LDI-200, degarelix, cintredelinbesudotox, FAVLD, MDX-1379, ISAtx-247, liraglutide, teriparatide (osteoporosis), tifacogin, AA4500, T4N5 liposome lotion, catumaxomab, DWP413, ART-123, CHRYSALIN®, desmoteplase, amediplase, corifollitropinalpha, TH-9507, teduglutide, DIAMYD®, DWP-412, growth hormone (sustained release injection), recombinant G-CSF, insulin (inhaled, AIR), insulin (inhaled, TECHNOSPHERE®), insulin (inhaled, AERX), RILONACEPT, DIAPEP277@, interferon beta (hepatitis C viral infection (HCV)), interferon alpha-n3 (oral), belatacept, transdermal insulin patches, AMG-531, MBP-8298, XERECEPT, opebacan, AIDSVAX, GV-1001, LYMPHOSCAN, ranpirnase, LIPOXYSAN, lusupultide, MP52 (beta-tricalciumphosphate carrier, bone regeneration), melanoma vaccine, sipuleucel-T, CTP-37, INSEGIA, vitespen, human thrombin (frozen, surgical bleeding), thrombin, TRANSMID, alfimeprase, PURICASE, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, ENDOSTATIN, ANGIOSTATIN, ABT-510, BOWMAN BIRK INHIBITOR CONCENTRATE, XMP-629, 99 mTc-Hynic-Annexin V, KAHALALIDE F, CTCE-9908, teverelix (extended release), ozarelix, rornidepsin, BAY-504798, interleukin4, PRX-321, PEPSCAN, iboctadekin, rhlactoferrin, TRU-015, IL-21, ATN-161, cilengitide, ALBUFERON, BIPHASIX, IRX-2, omega interferon, PCK-3145, CAP-232, pasireotide, huN901-DMI, ovarian cancer immunotherapeutic vaccine, SB-249553, ONCOVAX-CL, ONCO-VAX-P, BLP-25, CERVAX-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA®, OBI-1, AC-100, salmon calcitonin (oral, eligen), calcitonin (oral, osteoporosis), examorelin, capromorelin, CARDEVA, velafermin, 131I-TM-601, KK-220, T-10, ularitide, depelestat, hematide, CHRYSALIN® (topical), rNAPc2, recombinant Factor V111 (PEGylated liposomal), bFGF, PEGylated recombinant staphylokinase variant, V-10153, SonoLysis Prolyse, NEUROVAX®, CZEN-002, islet cell neogenesis therapy, rGLP-1, BIM-51077, LY-548806, exenatide (controlled release, MEDISORB®), AVE-0010, GA-GCB, avorelin, ACM-9604, linaclotid eacetate, CETi-1, HEMOSPAN, VAL (injectable), fast-acting insulin (injectable, VIADEL), intranasal insulin, insulin (inhaled), insulin (oral, eligen), recombinant methionyl human leptin, pitrakinra subcutancous injection, eczema), pitrakinra (inhaled dry powder, asthma), MULTIKINE®, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, TAUFERON, bile salt stimulated lipase, MERISPASE, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PEVIPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (NOVASOME®), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OXSODROL, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, PENTRYS, NORELIN, CYTOFAB, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, COMBOTOX, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (NOVASOME®), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, BIOSPHERE®), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenia disorders), AL-108, AL-208, nerve growth factor antagonists (pain), SLV-317, CGX-1007, INNO-105, oral teriparatide (eligen), GEM-OS1®, AC-162352, PRX-302, LFn-p24 fusion vaccine (THERAPORE), EP-1043, *S pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, VIADERM®), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA®), infliximab (REMICADE™), rituximab (RITUXAN™/MAB THERA™) etanercept (ENBREL™) bevacizumab (AVASTIN™), trastuzumab (HERCEPTIN™), pegrilgrastim (NEULASTA™), or any other suitable polypeptide including biosimilars and biobetters.

Other suitable polypeptides are those listed in Table 1 of US2016/0097074 and in Tables 1-3 of US2017/0260763.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged either in whole or in part. Furthermore, those of ordinary skill in the art will appreciate that the foregoing description is by way of example only, and is not intended to limit the invention so further described in such appended claims.

What is claimed:

1. A system for the growth of biologics comprising:
   a perfusion seed train or a fed-batch bioreactor seed train, wherein the perfusion seed train comprises at least one perfusion-based reactor;
   a bioreactor subsystem comprising at least two bioreactors fed from the perfusion seed train or the fed-batch bioreactor seed train, wherein the at least one perfusion-based reactor directly feeds at least one bioreactor of the at least two bioreactors;
   at least two harvest subsystems, wherein each harvest subsystem is configured to be in fluid communication with each of the bioreactors in the bioreactor subsystem individually or in combination, wherein the at least two harvest subsystems each comprise at least one harvest tank;
   at least one purification subsystem, wherein the at least one purification subsystem is configured to be in fluid communication with each of the at least two harvest subsystems individually or in combination, wherein the at least one purification subsystem is downstream from the at least two harvest subsystems, and further wherein a maintenance area is adjacent to the at least one purification subsystem and is directly accessible by airlocks and further wherein each of the at least one purification subsystem is directly accessible from the maintenance area by airlocks.

2. The system as defined in claim 1, further comprising a flow control assembly positioned in between the at least two bioreactors and the at least two harvest subsystems, the flow control assembly being configured to selectively control flow of a fluid from a first bioreactor to a first harvest subsystem and from the first bioreactor to a second harvest subsystem, the flow control assembly also being configured to control flow of a fluid from a second bioreactor to the first harvest subsystem and from the second bioreactor to the second harvest subsystem.

3. The system as defined in claim 1, wherein the system comprises at least two purification subsystems, wherein at least one purification subsystem is configured to produce a different biologic than at least one other purification subsystem.

4. The system as defined in claim 1, configured to process more than 100 batches per year.

5. The system as defined in claim 1, wherein at least one of the bioreactors is 6000 L or larger.

6. The system as defined in claim 1, wherein the bioreactor subsystem comprises at least one fed-batch bioreactor.

7. The system as defined in claim 1, wherein the at least two harvest subsystems feed at least two purification subsystems, wherein the at least two purification subsystems are operated in parallel.

8. The system as defined in claim 1, wherein the at least two bioreactors feed the at least two harvest subsystems, wherein the at least two harvest subsystems are operated in parallel.

9. The system as defined in claim 1, wherein the at least one purification subsystem comprises at least one chromatography column station.

10. The system as defined in claim 9, wherein the at least one purification subsystem comprises three chromatography column stations.

11. The system as defined in claim 1, wherein the at least one purification subsystem comprises a pre-viral train.

12. The system as defined in claim 11, wherein the pre-viral train comprises at least one chromatography column station.

13. The system as defined in claim 1, wherein the at least one purification subsystem comprises a post-viral train.

14. The system as defined in claim 13, wherein the post-viral train comprises at least one chromatography column station.

15. The system as defined in claim 1, wherein the at least one purification subsystem comprises a pre-viral train and a post-viral train, wherein the pre-viral train and the post-viral train are configured such that one of the pre-viral train and the post-viral train comprises at least one chromatography column station, wherein the at least one chromatography column station comprises at least one chromatography column, wherein the at least one chromatography column is configured such that it can be transferred from the pre-viral train to the post-viral train or from the post-viral train to the pre-viral train.

16. A system for the growth of biologics comprising:
a perfusion seed train or a fed-batch bioreactor seed train, wherein the perfusion seed train comprises at least one perfusion-based reactor;
a bioreactor subsystem comprising at least two bioreactors fed from the perfusion seed train or the fed-batch bioreactor seed train, wherein the at least one perfusion-based reactor directly feeds at least one bioreactor of the at least two bioreactors;
at least two harvest subsystems, wherein each harvest subsystem is configured to be in fluid communication with each of the bioreactors in the bioreactor subsystem individually or in combination, wherein each harvest subsystem is
downstream from the at least two bioreactors, wherein each harvest subsystem receives the effluent of the at least two bioreactors, wherein the at least two harvest subsystems each comprise at least one harvest tank;
at least one purification subsystem, wherein the at least one purification subsystem is configured to be in fluid communication with each of the at least two harvest subsystems individually or in combination, wherein the at least one purification subsystem is downstream from the at least two harvest subsystems, wherein the at least one purification subsystem comprises at least one chromatography column station;
a flow control assembly positioned in between the at least two bioreactors and the at least two harvest subsystems, the flow control assembly being configured to selectively control flow of a fluid from a first bioreactor to a first harvest subsystem and from the first bioreactor to a second harvest subsystem, the flow control assembly also being configured to control flow of a fluid from a second bioreactor to the first harvest subsystem and from the second bioreactor to the second harvest subsystem;
wherein the bioreactor subsystem, the at least two harvest subsystems, and the at least one purification subsystem are selectively operable such that one or more subsystems are operable while one or more subsystems are not operating, and further wherein a maintenance area is adjacent to the at least one purification subsystem and is directly accessible by airlocks and further wherein each of the at least one purification subsystem is directly accessible from the maintenance area by airlocks.

17. The system as defined in claim 16, wherein the at least one purification subsystem comprises three chromatography column stations.

18. The system as defined in claim 16, wherein the at least one purification subsystem comprises a pre-viral train.

19. The system as defined in claim 18, wherein the pre-viral train comprises the at least one chromatography column station.

20. The system as defined in claim 16, wherein the at least one purification subsystem comprises a post-viral train.

21. The system as defined in claim 20, wherein the post-viral train comprises the at least one chromatography column station.

22. The system as defined in claim 16, wherein the at least one purification subsystem comprises a pre-viral train and a post-viral train.

23. The system as defined in claim 22, wherein the pre-viral train and the post-viral train are configured such that one of the pre-viral train and the post-viral train comprises the at least one chromatography column station; wherein the at least one chromatography column station comprises at least one chromatography column, wherein the at least one chromatography column is configured such that it can be transferred from the pre-viral train to the post-viral train or from the post-viral train to the pre-viral train.

* * * * *